(12) United States Patent
Ricks-Laskoski et al.

(10) Patent No.: US 7,858,822 B1
(45) Date of Patent: Dec. 28, 2010

(54) POLYMERIZABLE SULFONATE IONIC LIQUIDS AND LIQUID POLYMERS THEREFROM

(75) Inventors: Holly L. Ricks-Laskoski, Springfield, VA (US); Arthur W Snow, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 12/862,281

(22) Filed: Aug. 24, 2010

Related U.S. Application Data

(62) Division of application No. 11/894,639, filed on Aug. 17, 2007, now Pat. No. 7,807,852.

(60) Provisional application No. 60/822,772, filed on Aug. 18, 2006.

(51) Int. Cl.
  *C07C 309/00* (2006.01)
(52) U.S. Cl. ....................................... 562/114
(58) Field of Classification Search ............... None
  See application file for complete search history.

(56) References Cited

PUBLICATIONS

Ricks-Laskoski et al., J. Am. Chem. Soc., 128, 12402-12403.*
Zhao et al., J. Chem. Technol. Biotechnol. 2005, 80, 1089.
Welton, Chem. Rev. 1999, 99, 2071.
Washiro, et al. Polymer, 2004, 45, 1577.
Ding, et al., J. Poly. Sci. Part A, 2004, 42,5794.
Tang, et al. J. Poly. Sci. Part A, 2005, 43, 5477.
Nakajima, et al., Polymer, 2005, 46, 11499.
Ogihara, et al., Electrochim. Acta, 2004, 49, 1797.
Binnemans, Chem. Rev., 2005, 105, 4148.
Anderson, et al., Anal. Chem. 2006, 78, 2893-2902.
Millefiorini,et al., J. Am. Chem. Soc. 2006, 128, 3098-3101.
Yoshizawa, et al., Polym. Adv. Technol. 2002, 13, 589-594.
Tang, et al., J. Poly. Sci.: Part A2005, 43, 1432-1443.
Quilliet, et a., Curr. Opin. Colloid Interface Sci. 2001, 6, 34-39.
Fisher, et al., Macromolecules, 1977, 10,949.
Bennett et al, Sensors and Actuators, 2004, 115, 79.

* cited by examiner

*Primary Examiner*—Karl J Puttlitz
(74) *Attorney, Agent, or Firm*—Amy L. Ressing; Joseph T. Grunkemeyer

(57) ABSTRACT

Disclosed is a new ionic liquid monomer salt and methods of is synthesis and polymerization. The ionic liquid monomer salt is prepared by mixing equimolar amounts of an amine, such as tris[2-(2-methoxyethoxy)-ethyl]amine and an acid functionalized polymerizable monomer, such as 2-acrylamido-2-methyl-1-propanesulfonic acid (AMPS), which is stirred at ambient temperature until salt formation is complete. Also disclosed is a new ionic liquid polymer salts and method for making the same. The synthesis of AMPS-ammonium salt polymer is accomplished by adding 2,2'-azobisisobutyronitrile (AIBN) to the ionic liquid monomer salt and heating the homogeneous melt at 70° C. for 18 hr.

3 Claims, 3 Drawing Sheets

POLYMERIZABLE SULFONATE IONIC LIQUIDS AND LIQUID POLYMERS THEREFROM

CROSS-REFERENCE TO RELATED APPLICATIONS

This Application is a Divisional of application Ser. No. 11/894,639 filed on Aug. 17, 2007. Application Ser. No. 11/894,639 claims the benefit of U.S. Provisional Application 60/822,772 filed on Aug. 18, 2006, both of which are incorporated herein by reference in their entirety.

BACKGROUND OF THE INVENTION

Ionic liquids are salts composed of cationic and anionic components whose structures impart a sub-room temperature melting point or glass transition to the resulting material. A liquid character is associated with ions that have very weak tendencies to coordinate toward oppositely charged ions (e.g. charge delocalized or sterically shielded), with substituents that have weak intermolecular forces (e.g. fluorocarbons, alkanes, silicones) and with a structural symmetry that is not conducive to efficient molecular packing. Most ionic liquids are organic salts. The cationic component is usually organic in nature (e.g. alkyl-substituted ammonium, phosphonium, imidazolium and pyridinium), and the anionic component is most often inorganic (e.g. nitrate, sulfate, thiocyanate, halide, tetrafluoroborate, hexafluorophosphate, etc.) but may also be organic (e.g. tosylate, alkylsulfates, fluoroalkylsulfates, alkylcarboxylates, fluoroalkylcarboxylates, etc.). These liquid materials have unique properties (immeasurably low volatility, non-flammability, very high polarity and solvating characteristics, high ionic conductivity, and a wide electrochemical potential window). There is currently much interest in their use as solvents for a large variety of reactions and in sampling for chemical analysis. See Zhao et al., J. Chem. Technol. Biotechnol. 2005, 80, 1089 and Welton, Chem. Rev. 1999, 99, 2071.

A more unique form of ionic liquid is based on a system where one of the two charged components is a polymer. As such, each repeat unit incorporates the same ionic site. There are very few reports in the literature of such systems. They are mostly based on the imidazolium ion functionalized with a polymerizable vinyl, acrylic or styryl moiety and have the physical form of a glass or sticky rubber. Reports include imidazolium polymers. See Washiro, et al. Polymer, 2004, 45, 1577; Ding, et al., J. Poly. Sci. Part A, 2004, 42, 5794; Tang, et al. J. Poly. Sci. Part A, 2005, 43, 5477; and Nakajima, et al., Polymer, 2005, 46, 11499 and alkali metal sulfonate polymers, see Ogihara, et al., Electrochim. Acta, 2004, 49, 1797 and Binnemans, Chem. Rev., 2005, 105, 4148. These polymers are prepared from monomers which themselves may or may not be ionic liquids. In the case of cationic imidazolium polymers, certain imidazolium monomer ionic liquids will yield the corresponding polymer ionic liquid if appropriate substitution is made on the imidazole ring; otherwise, a glassy solid is obtained. An appropriate substitution relates to the addition of a sufficient number and/or sufficient size of alkyl groups to the ring. In contrast, the anionic-form of a polymer ionic liquid has yet to be prepared directly from its analogous monomer ionic liquid. For instance, the high melting sulfonate monomer solid (usually an alkali metal salt) is first polymerized in solution followed by substitution with an appropriate cationic counter ion. Solvent removal is necessary to generate the anionic polymer liquid, still retaining the alkali metal ion.

Polymerizable ionic liquids and their actuation in an electric field are a combination of material and properties with unique potential to display structural and fluid dynamics above that found for small molecule ionic liquids. Small molecule ionic liquids are generally monovalent organic salts with melting points or glass transitions below room temperature. They derive their liquid character from a selection of ionic structures which have very weak tendencies to coordinate with oppositely charged ions, low intermolecular forces and low symmetry. Their properties (immeasurably low volatility, non-flammability, very high polarity and solvating characteristics, high ionic conductivity, and a wide electrochemical potential window) are of substantial interest particularly with regard to applications as green solvents, analytical extraction solvents, and electrochemical supporting media. Very recently it has been reported that water immiscible ionic liquids display significant electrowetting characteristics with an interesting dependence on the size of the cationic and anionic components. See Ralston, et al., J. Am. Chem. Soc., 2006, 126, 3098. Ionic liquids themselves provide an opportunity of producing a more stable actuating medium, eliminating such issues as solvent evaporation and degradation due to electrolysis, typically found in aqueous based electric field induced actuators.

In an ionic liquid polymer system the cationic or anionic centers are constrained to repeat units in the polymer chain. As such, any molecular flow or diffusion requires a concerted motion of as many ionic centers as there are charged repeat units in the polymer chain. When subjected to an electric field, a polymeric system may respond in an enhanced or retarded manner relative to a small molecule ionic liquid, depending on whether the covalent linkage of cationic or anionic repeat units responds as a more highly charged single molecule or whether its macromolecular size inhibits molecular motion needed for a response.

BRIEF SUMMARY OF THE INVENTION

Disclosed is a new ionic liquid monomer salt and methods of is synthesis and polymerization. The ionic liquid monomer salt is prepared by mixing equimolar amounts of an amine, such as tris[2-(2-methoxyethoxy)-ethyl]amine and an acid functionalized polymerizable monomer, such as 2-acrylamido-2-methyl-1-propanesulfonic acid (AMPS), which is stirred at ambient temperature until salt formation is complete. Also disclosed is a new ionic liquid polymer salts and method for making the same. The synthesis of AMPS-ammonium salt polymer is accomplished by adding 2,2'-azobisisobutyronitrile (AIBN) to the ionic liquid monomer salt and heating the homogeneous melt at 70° C. for 18 hr.

DETAILED DESCRIPTION OF THE INVENTION

Figure 1:
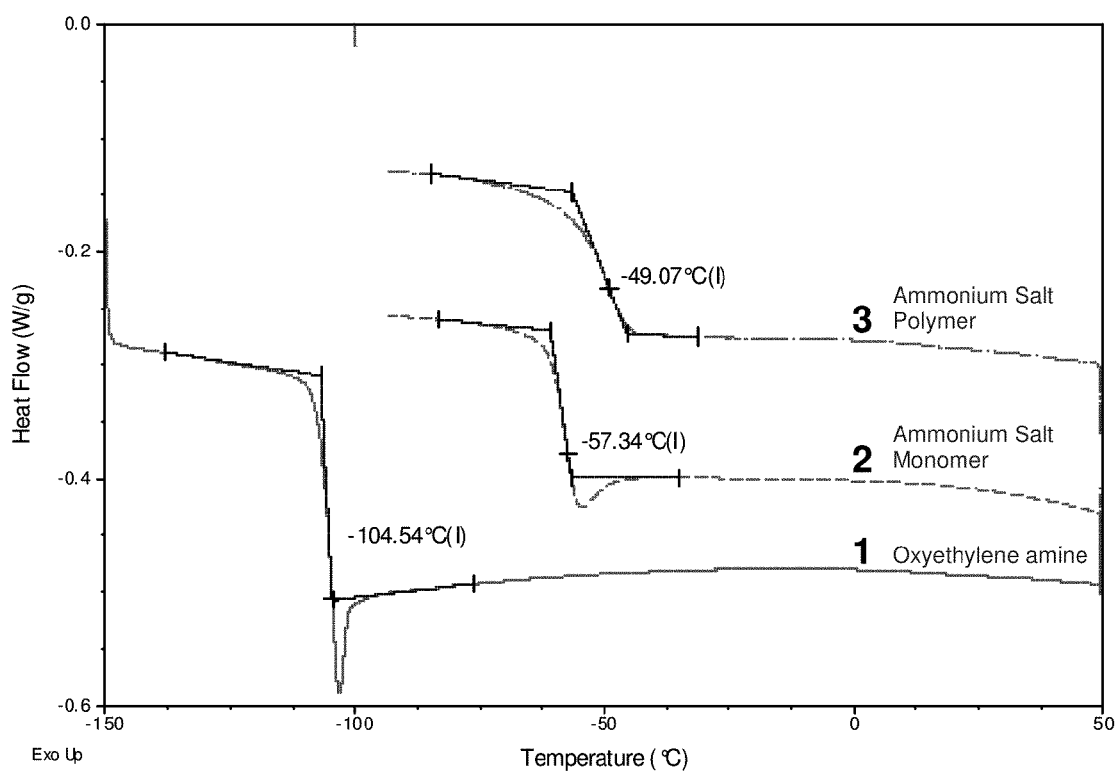
FIG. 1 is a differential scanning calorimetry comparison of oxyethylene amine, AMPS oxyethylene ammonium salt monomer, and polymer illustrating low Tg upon salt formation in the monomer and polymer.

Ionic liquid polymers and their actuation in an electric field are a combination of material and properties with unique potential to display structural and fluid dynamics above that found in small molecule ionic liquids. These structure and property dynamics are directly dependent upon an incorporation of a large number of positive or negative charges on the same polymer molecule while maintaining a liquid character under ambient conditions and a large temperature range where the polymer is a liquid or readily deformed viscoelastic solid. The strategy used in this invention for preparation of such polymers is to select acid functionalized monomer and organic base components that form acid-base salts that are liquids at room temperature and polymerize to form polymers that are also liquids at room temperature or, if lightly crosslinked, form very easily deformed viscoelastic solids. The acid functionality is selected as one having a strong acidity and one that is readily attached to polymerizable monomers. The sulfonic acid is particularly attractive although phosphoryl or carboxylic acids could also be made to serve this function. Functionalization of an acid group onto a polymerizable monomer such as a styrene, acrylate, olefin, vinyl ether, or acrylamide results in a relatively high temperature melting monomer. The 2-acrylamido-2-methyl-1-propanesulfonic acid (AMPS) monomer, used in the example, has a 192° C. melting point. Other commercially available monomers appropriate for this invention would include styrene sulfonic acid and vinyl sulfonic acid. Sulfonic acid functionalized monomers are the preferred class acid functionalized monomer with the AMPS monomer being the most preferred.

An organic base which has a very low melting point or glass temperature is selected so that it will depress the corresponding melting point or glass transition of the salt it forms with the acid monomer to an extent that its liquid range extends well below room temperature. For example, the organic base tris[2-(2-methoxyethoxy)-ethyl]amine, there are two oxyethylene groups in each amine substituent. These substituents cause the amine to have a very low glass transition, −104° C., and it is this low glass transition that causes the salt it forms with the AMPS monomer to also to have a low glass transition, −57° C. Other amines with similar characteristics (e.g. different numbers or mixed numbers of oxyethylene units) or with different substituents also correlating with low glass transitions (e.g. dimethylsiloxane and fluoromethylene) could work comparably. The amine base is the preferred organic base with the oxyethylene functionalized tertiary amine base being the most preferred. A physical mixing of the sulfonic acid functionalized monomer with the amine base generates the ionic liquid monomer salt which is then polymerized to form the corresponding ionic liquid polymer salt. Although not required, addition of a small amount of volatile solvent will promote a more rapid dissolution of the sulfonic acid functionalized monomer in the amine base; including, but not limited to methanol and ethylacetate.

A small quantity of polymerization catalyst is added to ionic liquid monomer salt to effect this transformation. The preferred catalysts are those that initiate free radical polymerization, and those that have high initiator efficiencies and solubility in the ionic liquid monomer salt are the most preferred. In cases where initiators need solubility, enhancement a small quantity of volatile, readily removable solvent such as methanol or ethyl acetate can be used to disperse the initiator in the monomer melt. The quantity of catalyst and the polymerization conditions used vary according to the specific characteristics of the catalyst and polymer molecular weight desired. A preferred catalyst, such as 2,2'-azobisisobutyronitrile, will typically be used in a quantity corresponding to a range of monomer:initiator ratio range of 50:1 to 1000:1 and under of temperature and reaction conditions of 50 to 110° C. and 3 to 24 hours respectively. An important feature of the monomer salt and of the ionic liquid polymer product is that they be a homogeneous melt throughout all stages of polymerization conversion. This feature results in the polymerization approaching quantitative conversions without an added solvent which would have to be subsequently separated. That the polymer product is also an ionic liquid qualifies it for unique electric field driven actuations such as physical shape changes, spreading on surfaces and droplet movement.

Provided are a composition of matter identified as an ionic liquid polymer salt, composed of an organic sulfonate repeat unit and a cationic organic counter ion and a general synthetic procedures for preparation of this class of compounds from ionic liquid monomers. Interest in such compositions of matter is driven primarily by electric field actuations in the form of electrowetting or Maxwell stress deformation of such materials. More specifically, an ionic liquid polymer system wherein a low molecular weight counter ion promotes an ionic liquid character in both the monomer salts and polymer salts and an observation of electrowetting where the polymer salt displays a distinctive effect relative to that for the monomer salt is disclosed. Disclosed is the preparation of a ionic liquid monomer salt, its solvent-free or solvent-assisted polymerization to the corresponding ionic liquid polymer salt, and an electrowetting wetting property that exceeds that of low molecular weight ionic liquids.

This new composition of matter is prepared utilizing a simple process; yet, retains much versatility for property development. By virtue of having a large number of ionic charges incorporated into a single polymer molecule which has liquid-like characteristics, this material has the capability of a unique response to an applied electric field. Advantages and new features reside in the accompanying properties and the applications they can support. Compared with low molecular weight ionic liquids, this material is capable of a large and polarity dependent response to an electric field. Applications that can take advantage of this property are actuators. In electronics it could find application as a dielectric material in a capacitor or perhaps as an electromigrating substance. Independent of the presence of an electric field, there are surface application possibilities such as a primer to improve surface wetting characteristics of low energy surface to accept paints and coatings of low polarity, as a biocidal treatment for surfaces, and as an adsorbent for opposite charged polyelectrolytes and possibly simple ionic species in chromatography columns. In solution this material could conceivably be used as a phase transfer agent or as a sequestrate for ionic substances. As a precursor to a polymer with different mechanical properties than a liquid, it could be converted to an elastomer or a flexible plastic and still retain its high ionic character.

In one embodiment, an ionic liquid monomer salt is provided, having the general formula:

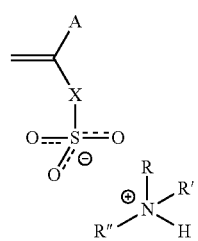

wherein:

A represents H or CH$_3$;

X represents —COY—, -p-C$_6$H$_4$—, -o-C$_6$H$_4$—, -m-C$_6$H$_4$—, —O—, or —CH$_2$—;

Y represents: —O(CH$_2$)$_n$—, where n=1 to 4, or

—(OCH$_2$CH$_2$)$_n$ where n=1 to 6, or

—NHCH(CH$_3$)—, —NHC(CH$_3$)$_2$—, —N(C$_{12}$H$_{25}$)CH$_2$CH$_2$—,

—NHC(CH$_3$)CH$_2$—, or —NHCH(C$_6$H$_5$)CH$_2$—, wherein each R, R', and R" can be the same group, or R can differ from R', while R' is the same group as R", or R, R', and R" may be all different groups; wherein R, R', R" each independently represented by one of the following:

—H, or

—(CH$_2$)$_n$CH$_3$ where n=1 to 12, or

—(CH$_2$CH$_2$O)$_n$CH$_3$ where n=1 to 4, or

—(CH)$_3$(Si(CH$_3$)$_2$O)$_n$CH$_3$ where n=1 to 6, or

—(CF$_2$)$_n$CF$_3$, —CH$_2$(CF$_2$)$_n$CF$_3$ where n=1 to 8.

Another embodiment of an ionic liquid monomer salt is presented, having the formula:

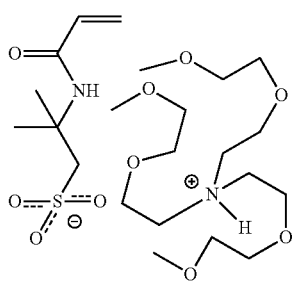

In another embodiment, an ionic liquid monomer salt is presented, having the formula:

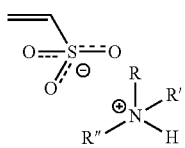

wherein each R, R', and R" can be the same group, or R can differ from R', while R' is the same group as R", or R, R', and R" may be all different groups; wherein R, R', R" each independently represented by one of the following:

—H, or

—(CH$_2$)$_n$CH$_3$ where n=1 to 12, or

—(CH$_2$CH$_2$O)$_n$CH$_3$ where n=1 to 4, or

—(CH)$_3$(Si(CH$_3$)$_2$O)$_n$CH$_3$ where n=1 to 6, or

—(CF$_2$)$_n$CF$_3$, —CH$_2$(CF$_2$)$_n$CF$_3$ where n=1 to 8.

In another embodiment, an ionic liquid polymer salt is presented, having the formula:

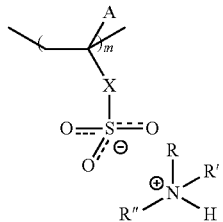

wherein m>1;

A represents H or CH$_3$;

X represents —COY—, -p-C$_6$H$_4$—, -o—C$_6$H$_4$—, -m-C$_6$H$_4$—, —O—, or —CH$_2$—;

Y represents:

—O(CH$_2$)$_n$— where n=1 to 4, or

—(OCH$_2$CH$_2$)$_n$ where n=1 to 6, or

—NHCH(CH$_3$)—, —NHC(CH$_3$)$_2$—, —N(C$_{12}$H$_{25}$)CH$_2$CH$_2$—

—NHC(CH$_3$)CH$_2$—, or —NHCH(C$_6$H$_5$)CH$_2$—, wherein each R, R', and R" can be the same group, or R can differ from R', while R' is the same group as R", or R, R', and R" may be all different groups; wherein R, R', R" each independently represented by one of the following:

—H, or

—(CH$_2$)$_n$CH$_3$ where n=1 to 12, or

—(CH$_2$CH$_2$O)$_n$CH$_3$ where n=1 to 4, or

—(CH)$_3$(Si(CH$_3$)$_2$O)$_n$CH$_3$ where n=1 to 6, or

—(CF$_2$)$_n$CF$_3$, —CH$_2$(CF$_2$)$_n$CF$_3$ where n=1 to 8.

In another embodiment, an ionic liquid polymer salt is presented, having the formula:

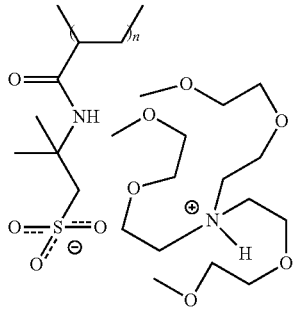

In another embodiment, an ionic liquid polymer salt is presented, having the formula:

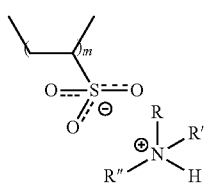

wherein m>1;

wherein each R, R', and R" can be the same group, or R can differ from R', while R' is the same group as R", or R, R', and R" may be all different groups; wherein R, R', R" each independently represented by one of the following:
—H, or
—(CH$_2$)$_n$CH$_3$ where n=1 to 12,
—(CH$_2$CH$_2$O)$_n$CH$_3$ where n=1 to 4,
—(CH)$_3$(Si(CH$_3$)$_2$O)$_n$CH$_3$ where n=1 to 6,
—(CF$_2$)$_n$CF$_3$, —CH$_2$(CF$_2$)$_n$CF$_3$ where n=1 to 8.

In another embodiment, a method for making an ionic liquid monomer salt is presented. An equimolar amount of a sulfonic acid functionalized monomer having the general formula:

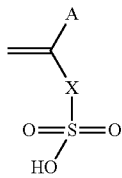

wherein A represents H or CH$_3$,
X represents —COY—, -p-C$_6$H$_4$—, -o-C$_6$H$_4$—, -m-C$_6$H$_4$—, —O—, or —CH$_2$—,
Y represents —O(CH$_2$)$_n$— where n=1 to 4, or
—(OCH$_2$CH$_2$)$_n$ where n=1 to 6, or
—NHCH(CH$_3$)—, —NHC(CH$_3$)$_2$—, —N(C$_{12}$H$_{25}$)CH$_2$CH$_2$—,
—NHC(CH$_3$)CH$_2$—, or —NHCH(C$_6$H$_5$)CH$_2$—,
is mixed with an organic amine base having the general formula:

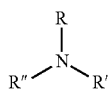

wherein each R, R', and R" can be the same group, or R can differ from R', while R' is the same group as R", or R, R', and R" may be all different groups; wherein
R, R', R" each independently represented by one of the following:
—H, or
—(CH$_2$)$_n$CH$_3$ where n=1 to 12, or
—(CH$_2$CH$_2$O)$_n$CH$_3$ where n=1 to 4, or
—(CH)$_3$(Si(CH$_3$)$_2$O)$_n$CH$_3$ where n=1 to 6, or
—(CF$_2$)$_n$CF$_3$, —CH$_2$(CF$_2$)$_n$CF$_3$ where n=1 to 8.

The mixture is stirred under an inert atmosphere until the sulfonic acid functionalized monomer is dissolved, wherein the dissolution completes formation of the ionic liquid monomer salt.

In another embodiment, a method for making an ionic liquid monomer salt is presented. An equimolar amount of a sulfonic acid functionalized monomer having the formula:

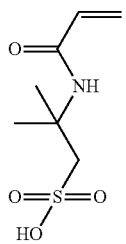

is mixed with an organic amine base having the formula:

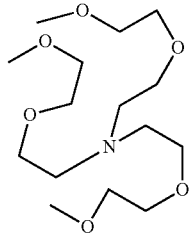

The mixture is stirred under an inert atmosphere until the sulfonic acid functionalized monomer is dissolved, wherein the dissolution completes formation of the ionic liquid monomer salt. Optionally, the ionic liquid monomer salt is in solvent methanol.

In another embodiment, a method for making an ionic liquid monomer salt is presented. An equimolar amount of a sulfonic acid functionalized monomer having the formula:

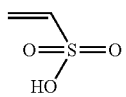

is mixed with the organic amine base having the general formula:

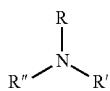

wherein each R, R', and R" can be the same group, or R can differ from R', while R' is the same group as R", or R, R', and R" may be all different groups; wherein
R, R', R" each independently represented by one of the following:
—H, or
—(CH$_2$)$_n$CH$_3$ where n=1 to 12, or
—(CH$_2$CH$_2$O)$_n$CH$_3$ where n=1 to 4, or
—(CH)$_3$(Si(CH$_3$)$_2$O)$_n$CH$_3$ where n=1 to 6, or
—(CF$_2$)$_n$CF$_3$, —CH$_2$(CF$_2$)$_n$CF$_3$ where n=1 to 8.

The mixture is stirred under an inert atmosphere until said sulfonic acid functionalized monomer is dissolved, wherein the dissolution completes formation of the ionic liquid monomer salt.

In another embodiment, a method for making ionic liquid polymer salts is presented. A free radical polymerization catalyst is added to an ionic liquid monomer salt having the general formula:

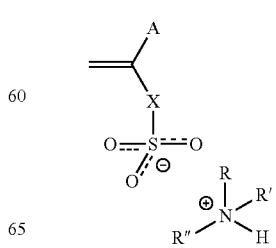

wherein A represents H or $CH_3$

X represents $-COY-$, $-p-C_6H_4-$, $-o-C_6H_4-$, $-m-C_6H_4-$, $-O-$, or $-CH_2-$ Y represents $-O(CH_2)_n-$ where n=1 to 4, or
$-(OCH_2CH_2)_n$ where n=1 to 6,
$-NHCH(CH_3)-$, $-NHC(CH_3)_2-$, $-N(C_{12}H_{25})CH_2CH_2-$,
$-NHC(CH_3)CH_2-$, or $-NHCH(C_6H_5)CH_2-$, wherein each R, R', and R" can be the same group, or R can differ from R', while R' is the same group as R", or R, R', and R" may be all different groups; wherein R, R', R" each independently represented by one of the following:

—H, or $-(CH_2)_nCH_3$ where n=1 to 12, or $-(CH_2CH_2O)_nCH_3$ where n=1 to 4, $-(CH)_3(Si(CH_3)_2O)_nCH_3$ where n=1 to 6, $-(CF_2)_nCF_3$, $-CH_2(CF_2)_nCF_3$ where n=1 to 8

The mixture is stirred under an inert atmosphere with application catalyst-specific polymerization conditions.

In another embodiment, a method for making ionic liquid polymer salts is presented. A free radical polymerization catalyst is added to an ionic liquid monomer salt having the formula:

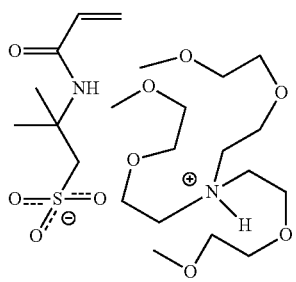

The mixture is stirred under an inert atmosphere with application catalyst-specific polymerization conditions. Optionally, the free radical polymerization can be conducted in solvent methanol. Preferably, the free radical polymerization catalyst is 2,2'-azobisisobutyronitrile and the monomer to free radical polymerization catalyst ratio is 100:1. The inert atmosphere is preferably a nitrogen atmosphere. The catalyst-specific polymerization conditions include heating the mixture to 70° C. and stiffing and heating steps are conducted for about 18 hours.

In another embodiment, a method for making ionic liquid polymer salts is presented. A free radical polymerization catalyst to said ionic liquid monomer salt claim 3 having the general formula:

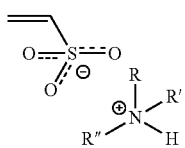

wherein each R, R', and R" can be the same group, or R can differ from R', while R' is the same group as R", or R, R', and R" may be all different groups; wherein R, R', R" each independently represented by one of the following:

—H, or $-(CH_2)_nCH_3$ where n=1 to 12, $-(CH_2CH_2O)_nCH_3$ where n=1 to 4, $-(CH)_3(Si(CH_3)_2O)_nCH_3$ where n=1 to 6, $-(CF_2)_nCF_3$, $-CH_2(CF_2)_nCF_3$ where n=1 to 8.

The mixture is stirred under an inert atmosphere with application catalyst-specific polymerization conditions.

This invention converts 1:1 mixture of a monomer having a polymerizable carbon-carbon double bond and a sulfonic acid or sulfonate group (such as 2-Acrylamido-2-methyl-1-propanesulfonic acid, AMPS, mp 192° C.) with an amine base (such as tris[2-(2-methoxyethoxy)-ethyl]amine) to an ionic liquid monomer salt that is polymerized to an ionic liquid polymer salt in the absence or presence of solvent. To convert the sulfonic acid monomer to a salt with a melting point or glass transition below room temperature, it complexed with an an amine is added. This amine is functionalized with large flexible substituent structures that depress a salt solidification temperature and inhibit coordination between oppositely charged species. Typical amine substituent structures involve oxyethylene oligomers, silicone oligomers, and fluorocarbon chains.

The synthesis is a two-step procedure as depicted below using the AMPS monomer and a tertiary amine with oxyethylene appendages of seven atoms as an example. Both steps proceed in remarkably good yields. The synthesis is detailed below in Scheme 1:

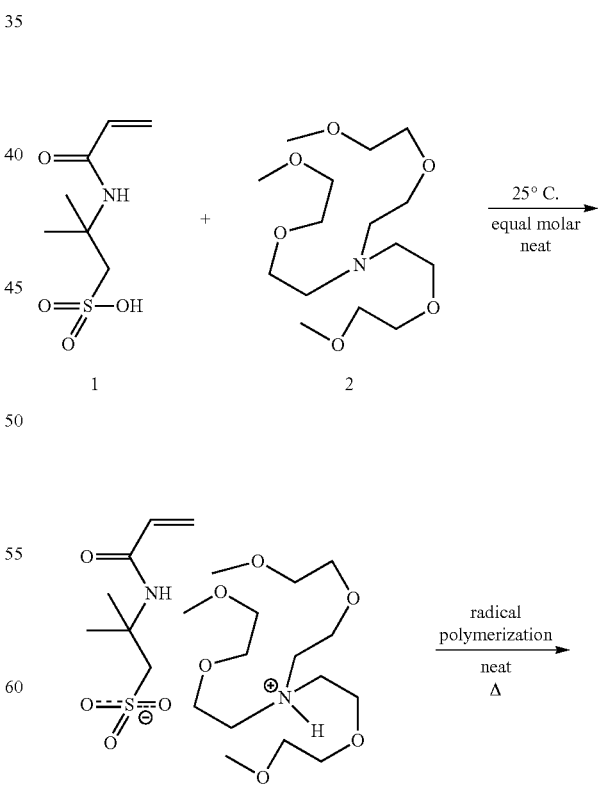

-continued

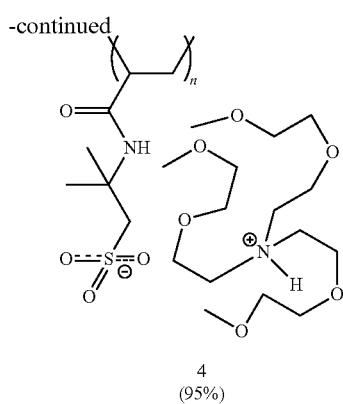

4
(95%)

Scheme 1 shows the synthesis commencing with the formation of the ammonium salt, 3. AMPS-oxyethylene ammonium salt monomer, 3, is synthesized by combining 2-acrylamido-2-methyl-1-propanesulfonic acid (AMPS), 1, with an equal molar quantity of freshly distilled tris[2-(2-methoxyethoxy)-ethyl]amine, 2, under an inert atmosphere, including but not limited to nitrogen or argon. The mixture is stirred for 8 hours at ambient temperature until the AMPS crystals are completely dissolved and converted into the monomer salt, 3, a slightly yellow viscous clear liquid. With no further purification necessary, a radical initiator such as 2,2'-azobisisobutyronitrile (AIBN) is added to the reaction flask utilizing air-free handling techniques under an inert atmosphere. The reaction mixture is heated to 70° C. and reacted for 18 hrs. The transparent amber ionic liquid polymer salt, 4, may be used as is or further purified to remove a small percentage (<5%) of unreacted monomer by dissolving in acetone and reprecipitating in cold diethyl ether. This precipitate is collected by cold suction filtration and upon warming, becomes a tacky transparent yellow liquid. The glass transition temperatures of the oxyethylene amine, 2, AMPS monomer salt, 3, and polymer ionic liquid, 4, are −104, −57, and −49° C. respectively. Infrared, and NMR spectral analyses— are consistent with the polymer repeat unit structure. The intrinsic viscosity value of 0.3 is indicative of a low, but significant molecular weight. Electrowetting characterization displays a reversible contact angle change from 75° to 30° with an applied voltage change from 0 to 157 volts. This change is larger than that of the monomer salt or of commercial ionic liquids. Those skilled in the art would understand that other radical initiators can be used, and the time and temperature of the reaction would vary depending upon the initiator chosen.

The properties of this ionic liquid polymer salt can be tuned by varying the identity, size and symmetry of the substituents on the amine counter ion or by varying the structure and function of the sulfonated monomer; such that, the monomer itself could go from being a repeat unit to a branch point to a crosslink.

These and other features and advantages of the present invention will be presented in more detail in the following specification of the invention and the accompanying figures, which illustrate, by way of multiple examples, the principles of the invention.

Example

The formation of the ionic liquid monomer salt and its polymerization is depicted in Scheme 1. The polymerizable component is the 2-acrylamido-2-methyl-1-propanesulfonic acid (AMPS) monomer which is a crystalline compound with a 192° C. melting point. It is converted to a liquid ammonium salt by addition of an equimolar quantity of tris[2-(2-methoxyethoxy)-ethyl]amine. This tertiary amine was selected as one that would solvate the AMPS monomer without the need of a solvent and one whose oxyethylene substituents would shield the protonated ionic center from coordinating with the sulfonated anion, thereby depressing the melting point or glass transition to a very low temperature.

The glass transitions of the free amine 2 (−104° C.) and of the AMPS-ammonium salt 3 (−57° C.) presented in the differential scanning calorimetry (DSC) thermogram in FIG. 1 demonstrate the remarkable capability of the oxyethylene substituted amine to extend the liquid range of a salt to low temperatures. After the liquid ammonium sulfonate monomer formation is complete, a free radical initiator (2,2'-azobisisobutyronitrile, AIBN) is added and reacted at 70° C. The monomer conversion is 95%, and the product is a clear acetone-soluble viscous liquid. The spectroscopic characterization (IR, $^1$H and $^{13}$C NMR) is consistent with polymer structure depicted in Scheme 1. The molecular weight is low but significant as indicated by an intrinsic viscosity measurement of 0.30 which is uncorrected for an observed polyelectrolyte coil expansion effect. The glass transition temperature of ionic liquid polymer 4 is −47° C. as depicted in the FIG. 1 thermogram. This is a remarkably modest increase from that of the unpolymerized monomer salt.

Figure 2:
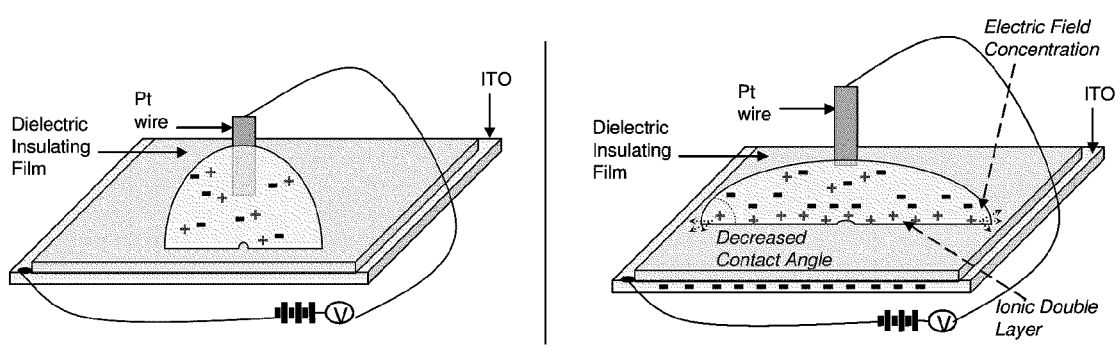
FIG. 2 is a depiction of an electrowetting actuation electrode setup with (right) and without (left) an induced electric field.

Electrowetting is an electrostatically driven surface effect where a liquid droplet's spreading on a hydrophobic surface is modulated by application of a voltage to the droplet and an underlying conducting substrate. A schematic of this effect is illustrated in FIG. 2. The droplet rests on a very thin low-dielectric insulating film (Teflon AF) which is supported on a conducting substrate and is contacted at the top by a very fine wire contact. Application of a voltage builds up a layer of charge on both sides of the interface with the dielectric film and decreases the interfacial energy.

Figure 3:
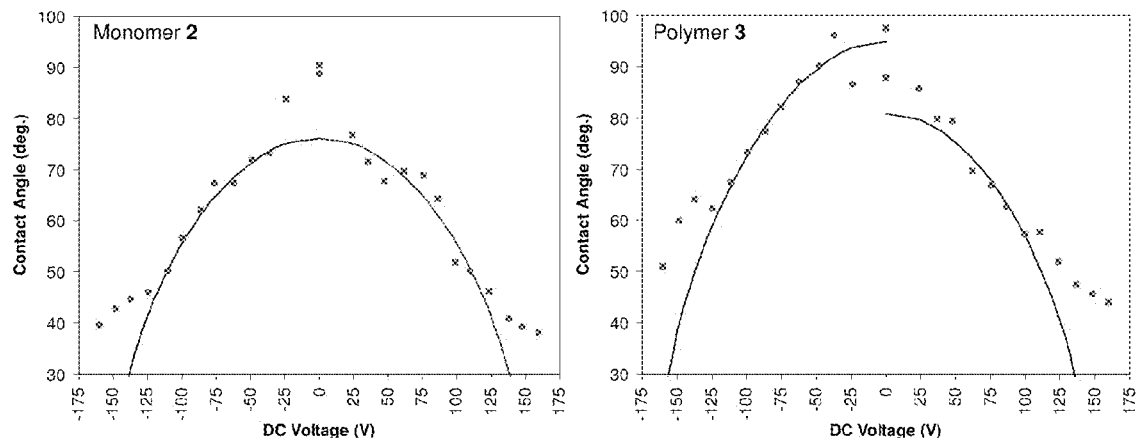
FIG. 3 shows electrowetting curves of monomer (left) and polymer.
Figure 4:
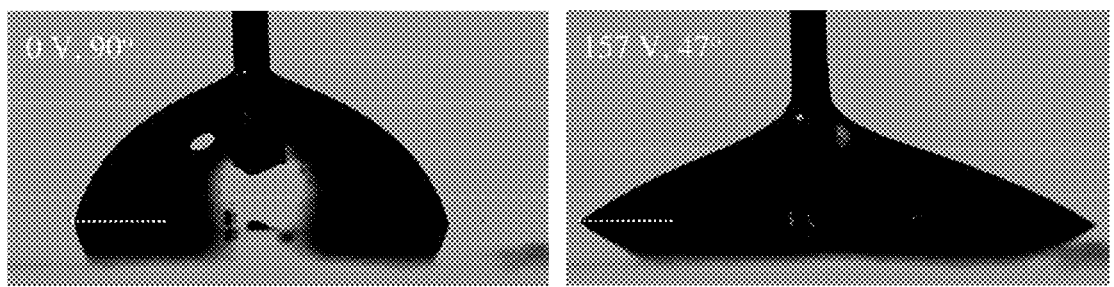
FIG. 4 shows electrowetting AMPS oxyethylene ammonium salt polymer as voltage increase from 0 V (left) to 157 V (right).

The observed response is a spreading of the droplet and a changing of its curvature. The dependence of the droplet's contact angle, θ, on the applied voltage, V, is described by the Young-Lippmann equation as follows (Equation 1):

$$\cos\theta = \cos\theta_0 + \frac{1}{2\gamma}CV^2 = \cos\theta_0 + \frac{\varepsilon\varepsilon_0}{2\gamma t}V^2$$

where $\theta_0$ is the contact angle at zero voltage, C is the capacitance per unit area, γ is the surface tension of the liquid, ∈ is the permittivity of the insulating dielectric, $\in_0$ is the electric constant and t is the thickness of the dielectric layer. Surface tension measurements of the monomer 3 and polymer 4 are 38.1 and 47.0 mJ/m$^2$ respectively. The contact angle measurements of the AMPS-ammonium salt monomer 3 and polymer 4 as a function of applied DC voltage are shown in FIG. 3, and photographs of the ionic liquid polymer droplet at zero and maximum applied voltages in FIG. 4 show a substantial contact angle change.

A parabolic best fit of the experimental contact angles to the voltage dependence of Equation 1 is represented by the continuous line. A parabolic best fit of the experimental contact angles to the voltage dependence of Equation 1 is represented by the continuous line in FIG. 3. Separate best fits were made for the negative and positive voltage regions of the curves. The electrowetting curve for the AMPS-ammonium sulfonate monomer, 3, is similar to those reported for small molecule ionic liquids in both magnitude and shape. No evolution of gas bubbles, discoloration, or degradation was observed between 0 and 157 V.

A monomer vs. polymer comparison of contact angle data for AMPS-ammonium salt system presents an interesting contrast. The polymer displays a larger contact angle at zero voltage; a similar magnitude of contact angle change over the voltage range; a departure from the Young-Lippmann equation at a lower voltage; and a dissymmetry between the negative and the positive voltage sections of the electrowetting curve.

These observed differences in electrowetting behavior correlate with the higher surface tension of the polymer and with the polyelectrolyte molecular structure. When no voltage is applied, the greater surface tension of the polymer is clearly consistent with the larger contact angle observed. When a voltage is applied, an electric field is concentrated across the Teflon AF interface and an ionic double layer of charge forms in the liquid at this interface. This decreases the surface tension at the solid-liquid interface and results in spreading of the liquid on the charged surface. A depiction is illustrated in FIG. 2. The polymer differs from the monomer in that one of the charged components is a small cationic molecule and the other is a large anionic polyelectrolyte. When the substrate is charged, an oppositely charged component of the ionic liquid is adsorbed at the Teflon AF-ionic liquid interface. On reversal of polarity, a grouping of small molecule ions exchanges position with the polyelectrolyte. This disparity of molecular size correlates with the dissymmetry observed between the positive and negative sides of the electrowetting curve in FIG. 3.

All $^1$H-HMR spectroscopy were obtained using a Bruker AC-300 spectrometer using d6-DMSO as solvent. FTIR spectra were obtained using a Nicolet Magna-IR 750 spectrometer with sample supported on a NaCl plate under a nitrogen purge of 40 cm$^3$ min$^{-1}$. All differential scanning calorimetric (DSC) analysis were performed on a TA Instruments DSC Q100 Modulated thermal analyzer at a heating rate of 10° C. min-1 and a nitrogen purge of 25 cm3min-1.

Synthesis of AMPS-ammonium salt monomer. A nitrogen purged 50 ml schlenk flask was charged with freshly distilled tris[2-(2-methoxyethoxy)-ethyl]amine (1.69 g, 5.24 mmol) and 2-acrylamido-2-methyl-1-propanesulfonic acid (AMPS) (1.09 g, 5.24 mmol) and stirred at ambient temperature for 8 hr or until completely dissolved. Total dissolution completes formation of the AMPS-ammonium salt monomer as a transparent light amber oil in a 99% yield which was used immediately without further purification.

Synthesis of AMPS-ammonium salt polymer. To the prepared monomer was added 2,2'-azobisisobutyronitrile (AIBN) (6.0 mg, 0.04 mmol) under a nitrogen purge. The reaction flask was then sealed, allowed to vent to a bubbler, and heated to 70° C. for 18 hr. Upon cooling to ambient temperature, the transparent dark amber mixture was dissolved in acetone (10 ml) and precipitated as white flocculants into cold diethyl ether (50 ml) (dry ice/acetone bath) and quickly collected in a dry ice cooled Buchner funnel via suction filtration. As the material warmed, the flocculants became a transparent amber oil which was then dried under vacuum to remove any residual solvents to yield polymer (95%).

Electrowetting actuation setup and experimentation. Actuation was measured using the following setup as illustrated in FIG. 2: a VCA OptimaXE commercial contact angle instrument fitted with a stage was used to capture individual data points at various DC voltages. An ITO coated slide, was spin-coated with Teflon AF (DuPont) at 2000 rpm for 30 seconds and heat treated in an oven at 80° C. for 18 hr which produced an insulating film with a thickness of 1.29 µm (determined by a KLA Profilometer) with an intrinsic roughness on the order of 0.5 µm. The ITO slide was coupled to an electrode in an area which was absent of Teflon AF and a Pt wire with a diameter of 0.25 mm was used as the corresponding top electrode. Small aliquots of ionic liquid monomer (3) or polymer (4) (~50 µl) were placed onto the ITO/Teflon AF coated slide in droplet form. The Pt electrode was inserted into the droplet and snapshots were taken at ~8 V intervals from 0 to 157 V (DC) with polarities of the electrodes being reversed to obtain measurements between −157 and 0 V (DC) with respect to the ITO electrode. Contact angle software, from AST Products, Inc. VCA Version 1.90.0.9 for Windows, calculated left and right advancing angles for both the AMPS oxyethylene ammonium salt monomer 3 and polymer 4, which are plotted over a voltage range in FIG. 3. The voltage polarity corresponds to the ITO electrode. No discoloration, etching, or insoluble residue was resultant from these experiments involving ionic liquid 3 and 4 nor was it observed on the ITO surface itself. Once a voltage of 157 was reached (for either polarity), receding contact angles were recorded as the voltage was slowly decreased back to 0.

Surface Tension Measurements: Surface tensions for both the monomer (3) and polymer (4) were measured at 23° C. by the pendant drop method using the VCA contact angle instrument and Pendant Analysis Software (Version 2.22) and found to be 38.1 and 47.0 mJ/m2, respectively; higher than those previously reported for other ionic liquids. To further address this issue, the surface tensions of structurally relevant compounds are considered. The surface tension of the free amine (tris[2-(2-methoxyethoxy)-ethyl)amine, 2 was measured at 32.8 mJ/m2 (23° C.). As a representative of a liquid organic sulfonic acid, methane sulfonic acid has a surface tension of 50.2 mJ/m2 [Lange's Handbook of Chemistry, 15th Ed., J. A. Dean, 1999]. A complex formed between these two components would probably have an intermediate value assuming little contribution from the ammonium sulfonate salt formation. As such this ammonium-hydrogen-sulfonate ionic liquid is somewhat different from other ionic liquids including those for which surface tensions have been reported in that significant hydrogen bonding is incorporated into it. We would speculate that the hydrogen bonding would elevate the surface tension. We would further speculate that transformation of the AMPS-ammonium salt monomer 3 to polymer 4 would enhance the density of the hydrogen bonding and further elevate the surface tension as observed. Hence, we speculate that a more dense structure of the polymer and hydrogen bonding is consistent with an increased surface tension.

This example represents synthesis and electrowetting of individual members of new ionic liquid monomer and polymer systems. The uniqueness of the oxyethylene amine formation of the ammonium cationic species contributes to both the ionic and liquid nature of the monomer and polymer. Even more remarkable is the ability of this polymer to maintain its liquid nature after polymerization and wet a substrate, showing preference for one polarity based upon the makeup of the ionic backbone of the polymer formed.

Obviously, many modifications and variations of the present invention are possible in light of the above teachings. It is therefore to be understood that, within the scope of the appended claims, the invention may be practiced otherwise than as specifically described.

What is claimed as new and desired to be protected by Letters Patent of the United States is:

1. An ionic liquid monomer salt having the formula:

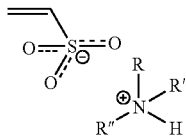

wherein R, R', and/or R" are each independently selected from H, or
- —$(CH_2)_n CH_3$ where n=1 to 12, or
- —$(CH_2CH_2O)_n CH_3$ where n=1 to 4, or
- —$(CH)_3(Si(CH_3)_2O)_n CH_3$ where n=1 to 6, or
- —$(CF_2)_n CF_3$, —$CH_2(CF_2)_n CF_3$ where n=1 to 8.

2. A method for making an ionic liquid monomer salt comprising:

mixing an equimolar amount of a sulfonic acid functionalized monomer having the formula:

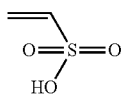

with the organic amine base having the general formula:

wherein R, R', and/or R" are each independently selected from H, or
- —$(CH_2)_n CH_3$ where n=1 to 12, or
- —$(CH_2CH_2O)_n CH_3$ where n=1 to 4, or
- —$(CH)_3(Si(CH_3)_2O)_n CH_3$ where n=1 to 6, or
- —$(CF_2)_n CF_3$, —$CH_2(CF_2)_n CF_3$ where n=1 to 8; and stiffing said mixture under an inert atmosphere until said sulfonic acid functionalized monomer is dissolved, wherein the dissolution completes formation of the ionic liquid monomer salt.

3. A method for making an ionic liquid polymer salt comprising:

providing the ionic liquid monomer salt claim 1 having the general formula:

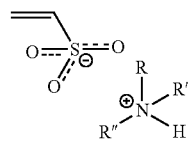

wherein R, R', and/or R" are each independently selected from H, or
- —$(CH_2)_n CH_3$ where n=1 to 12, or
- —$(CH_2CH_2O)_n CH_3$ where n=1 to 4, or
- —$(CH)_3(Si(CH_3)_2O)_n CH_3$ where n=1 to 6, or
- —$(CF_2)_n CF_3$, —$CH_2(CF_2)_n CF_3$ where n=1 to 8;

adding a free radical polymerization catalyst to said ionic liquid monomer salt;

stiffing said mixture under an inert atmosphere with application catalyst-specific polymerization conditions.

* * * * *